Figure 1:
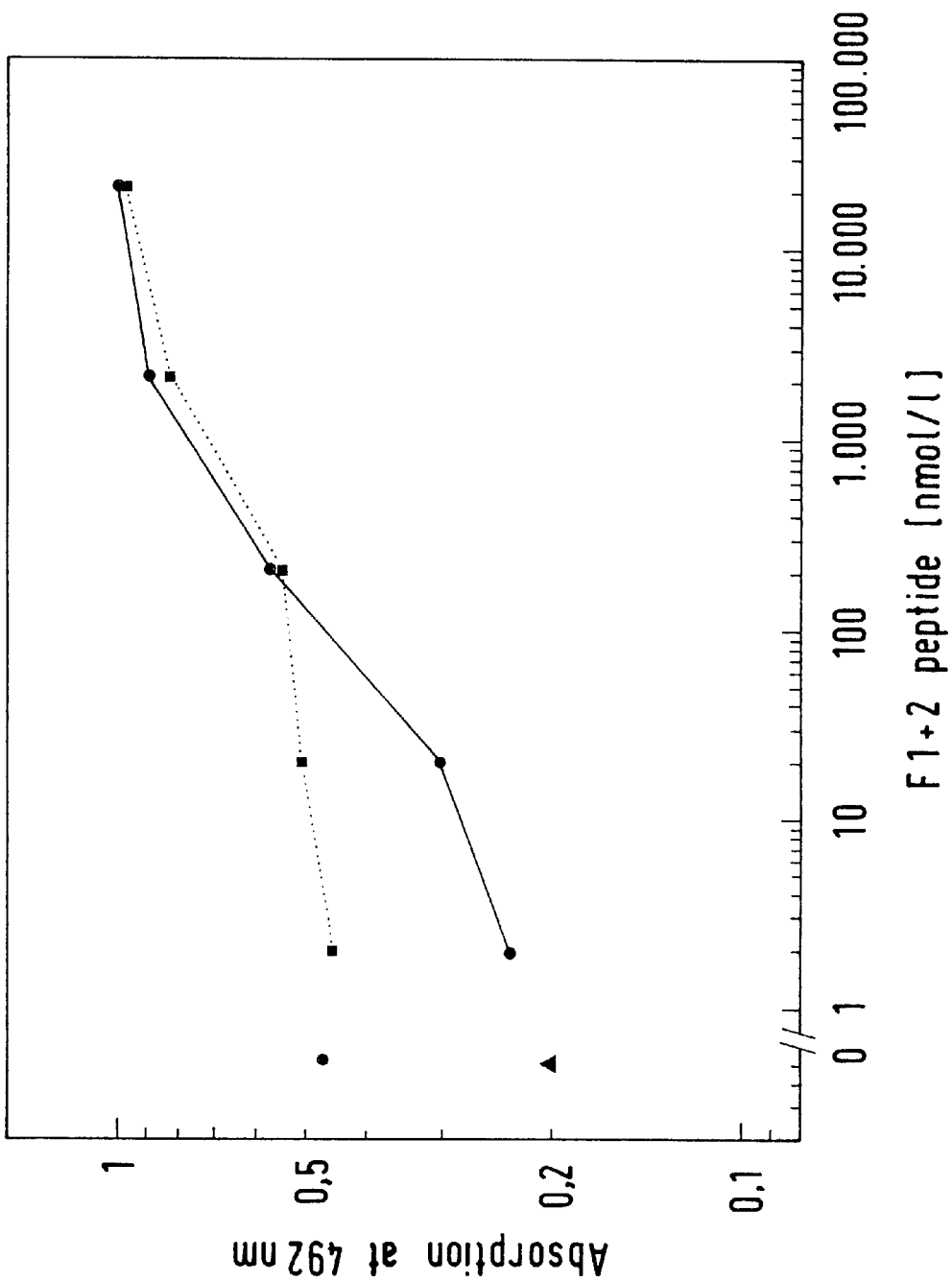

United States Patent [19]
Kraus

[11] Patent Number: 6,143,575
[45] Date of Patent: *Nov. 7, 2000

[54] HETEROGENEOUS IMMUNOASSAY USING A PRECIPITABLE SOLID PHASE

[75] Inventor: Michael Kraus, Marburg, Germany

[73] Assignee: Dade Behring Marburg GmbH, Marburg, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/554,306

[22] Filed: Nov. 8, 1995

[30] Foreign Application Priority Data

Nov. 12, 1994 [DE] Germany ............... 44 40 487

[51] Int. Cl.⁷ .................................. G01N 33/533
[52] U.S. Cl. .................. 436/518; 435/7.1; 435/7.24; 435/7.25; 435/7.5; 435/7.8; 435/7.9; 435/7.93; 435/7.94; 435/525; 435/526; 435/527; 435/529; 435/530; 435/539; 436/518; 436/519; 436/520; 436/523
[58] Field of Search ..................... 435/7.1, 7.24, 435/7.25, 7.5, 7.8, 7.9, 7.93, 7.94; 436/518–520, 523, 525, 526, 527, 529, 530, 539

[56] References Cited

U.S. PATENT DOCUMENTS

| | | | |
|---|---|---|---|
| 4,554,088 | 11/1985 | Whitehead et al. | 252/62.54 |
| 4,556,642 | 12/1985 | Collet-Cassart et al. | 436/500 |
| 4,590,169 | 5/1986 | Cragle et al. | 436/523 |
| 4,636,479 | 1/1987 | Martin et al. | 436/533 |
| 4,720,465 | 1/1988 | Jensen et al. | |
| 4,829,011 | 5/1989 | Gibbons | 436/512 |
| 5,071,774 | 12/1991 | Vorpahl et al. | 436/501 |
| 5,445,936 | 8/1995 | Piran et al. | 435/6 |

FOREIGN PATENT DOCUMENTS

| | | |
|---|---|---|
| 0 161 107 A2 | 11/1985 | European Pat. Off. |
| 0 345 777 A2 | 12/1989 | European Pat. Off. |
| 63-85358 | 4/1988 | Japan. |
| WO90/01559 | 2/1990 | WIPO. |
| WO92/22201 | 12/1992 | WIPO. |

OTHER PUBLICATIONS

Kapmeyer et al., "Automated Nephelometric Immunoassays With Novel Shell/Core Particles", Journal of Clinical Laboratory Analysis, 2:76–83(1988).

Tijssen, P., "Practice and Theory of Enzyme Immunoassays", Laboratory Techniques In Biochemistry and Molecular Biology, vol. 15, (1988). (Title page, Preface and Contents pages enclosed).

Harbron et al., "Amplified Assay of Alkaline Phosphatase Using Flavin–adenine Dinucleotide Phosphate as Substrate", Analytical Biochemistry, 206:119–124 (1992).

Rattle et al., "New Separation Method For Monoclonal Immunoradiometric Assays and Its Application to Assays for Thyrotropin and Human Choriogonadotropin," Clin. Chem. 30 (9):1457–61 (1984).

European Search Report, dated Mar. 14 1996.

*Primary Examiner*—Christopher L. Chin
*Assistant Examiner*—Bao-Thuy L. Nguyen
*Attorney, Agent, or Firm*—Finnegan, Henderson, Farabow, Garrett & Dunner, L.L.P.

[57] ABSTRACT

The invention relates to a method for carrying out heterogeneous immunoassays, in particular to a method for separating a coated solid phase from a liquid phase by means of precipitation and subsequent centrifugation, with a detectable activity remaining in the liquid phase.

25 Claims, 7 Drawing Sheets

HETEROGENEOUS IMMUNOASSAY USING A PRECIPITABLE SOLID PHASE

The invention relates to a method for carrying out heterogeneous immunoassays, in particular to a method for separating a coated solid phase from a liquid phase by precipitation and subsequent centrifugation, with a detectable activity remaining in the liquid phase.

Immunochemical methods are frequently used to detect analytes, for example antibodies, which are only present in low concentrations in biological fluids but whose detection is important for the diagnosis and therapy of diseases.

In immunological determination methods, a distinction is made between homogeneous and heterogeneous methods. In homogeneous methods, the binding partners are not separated prior to the detection reaction whereas, in heterogeneous methods, the binding reaction and the detection reaction take place one after the other, after the physical separation of the binding and detection partners. While homogeneous detection methods, for example the measurement of turbidity in particle-amplified agglutination methods, are often faster to carry out, they are often more susceptible to interference and less sensitive than heterogeneous methods owing to the absence of the separation step.

In addition, a distinction is made between direct and competitive detection methods. In direct detection methods, the binding reaction and the detection reaction take place on the analyte, for example by binding it to a first antibody on the solid phase and by binding a conjugate of a second antibody, which conjugate carries a detectable constituent, to this complex, for example sandwich assays. In competitive detection methods, by contrast, the analyte of the sample competes with a labeled analyte or an analyte-like compound for binding to a solid phase which can, for example, be coated with an analyte-specific antibody. The competition can be detected either in a homogeneous system, for example by inhibiting the agglutination reaction, or in a heterogeneous system, for example by determining the quantity of the labeled analyte which is bound to the solid phase. Such competitive methods are advantageously used to detect analytes having only one specific binding site or in the case of very small molecules (haptens) which only permit one binding reaction and not two binding reactions (solid phase and conjugate) as are required in the case of direct detection methods.

The detection of proteins having only one characteristic epitope, as well as the detection of haptens, place special demands on the design of the test. Thus, homogeneous immunoassays in accordance with the agglutination principle, for example, are, at most, possible in a competitive design. Since the sensitivity of these assays is usually low, as discussed at the outset, heterogeneous methods are required. For separating analyte or analyte conjugate which is bound and still in solution, conventional heterogeneous immunological methods make use of binding partners which are complementary to the analyte and which have been immobilized on a support, for example small tubes or microtitration plates, and which can therefore be washed. In the further development of heterogeneous methods, it is advantageous to use pipettable solid phases since these render it possible to determine different analytes in different amounts ("random access"). Coated particles, for example, are used as pipettable solid phases.

Thus, DE 41 26 436, for example, has described the use in immunochromatography of antibodies which are coupled to agarose particles for bringing about the immunochemical isolation of analytes. Besides this, further methods have been described in which coated microparticles are used for separating analytes. These methods differ from each other in the manner in which separation of the coated particles is effected.

Separation by filtering the microparticle suspension in the solution to be investigated has also previously been described, for example in DE 41 24 778. A similar approach can also be taken in the case of a competitive immunoassay. That which is determined is either the quantity of the analyte remaining on the solid phase or, in competitive methods, the free analyte/enzyme conjugates remaining in the filtrate. In an additional variant, the analyte/enzyme conjugates remaining in the immune complexes are liberated once again and the activity of the enzyme is determined.

A method has also been described in which coated particles are separated off manually after they have been brought into contact with the analyte-containing solution and are washed before the bound analyte is subjected to further analysis.

For example, US (91/716,144) describes how coated magnetic particles are immobilized by the proximity of magnets and can in this way be washed before the bound analyte is subjected to further analysis.

All these methods which have been described require equipment which is specifically geared to the separation systems. There was, therefore, the need for a method of separating the solid phase which can also be applied to current clinicochemical analyzers without the need for any special washing and/or separating devices.

In JP 86-230925, the analyte is bound, in the presence of analyte/enzyme conjugate, to antibody-coated polystyrene particles which are separated out of the reaction solution, and washed, by centrifugation. The enzyme activity of the precipitate is determined. However, this method requires very high centrifugal forces and cannot, therefore, be used on current centrifugal analyzers. In addition to this, the method which is described requires a separate washing step. Current centrifugal analyzers operate with maximum accelerations of up to approximately 1500× g.

In JP 88-143257, a mixture composed of coated particles which are directed against the analyte and of antibody conjugate is formed, in a direct method, and this mixture is left to stand with the analyte-containing solution for several hours at room temperature. The soluble activity of the antibody conjugate remaining in the supernatant is then determined separately. Apparently, although the method description does not go into this point, the resulting complexes composed of particle-analyte-anti-analyte/conjugate sediment during the long incubation period so that the anti-analyte/conjugate is depleted in the supernatant to an extent corresponding to the quantity of free analyte. This method is extremely unsatisfactory since the period required for sedimentation necessitates extremely long incubation times and these conjugate-containing complexes can also become involved in the conjugate determination due to mechanical vibrations or to variations in the depth of immersion of the pipetting arm.

In GB 84-11706, a mixture composed of analyte (a hapten), anti-analyte antibody/label 1 conjugate and analyte/label 2 conjugate is separated such that, in a first incubation, complexes are formed from the anti-analyte antibody label 1 conjugate together with the free analyte or, competitively, together with the analyte/label 2 conjugate. The bound analyte/label 2 conjugate is separated, in a further step, by immobilizing it on a solid phase by means of binding the label 1. For this purpose, small tubes, in particular, are used which are coated with antibodies directed against label 1. In another variant, antibodies against label 1 are first added followed by kaolin which is coated with antibody against these anti-label 1 antibodies. In this second variant, separation is achieved by means of centrifugation. The activity of the label 2 is then detected in the precipitate, which additionally has to be washed in order to eliminate corresponding carry-over from the solution. This method is very complex. Thus, antibodies from 3 different species are employed in the second variant. In accordance with this, the incubation times which are required add up to several hours. Furthermore, this method is limited to the detection of haptens.

Although some of the previously described methods are already in practical use, it has been found that none of the customary methods is optimally suitable for use in current centrifugal analyzers.

The technical problem underlying the present invention was consequently to find a heterogeneous immunochemical detection method which is suitable for use in one of the current centrifugal analyzers.

This technical problem is solved by the provision of the embodiments described in the patent claims such as embodiments wherein the analyte has been prepared by genetic or synthetic manipulation or wherein the precipitation substance is directed against a substance which is additionally coupled to the first, unlabeled specific binding partner. Another embodiment comprises a method wherein the precipitation substance is itself immobilized on an insoluble solid phrase. Yet in another, the first, unlabeled specific binding partner is not bound to a solid phase. Still another embodiment requires that the solid phase is selected from a group of particles such as glass, gelatine, agarose, lipids, erythrocytes, blood platelets, leucocytes, metal colloids and synthetic materials, which are preferably magnetizable and may be selected from the group consisting of polystyrene, polydextran, polypropylene, polyvinyl chloride, polyvinylidene fluoride, polyacrylamide or styrene-butadiene, styrene-methacrylic acid or methacrylate-methacrylic acid copolymers. In a still further embodiment, the binding partner comprises at least one of the following substances: antibody, lectin, avidin, streptavidin, biotin, or derivatives thereof, complement factor C1, mannan-binding protein or a cofactor. Finally, another embodiment employs magnetizable particles as the pipettable, particulate solid phase and magnetic particles as the precipitation substances or vice versa.

It has been observed, surprisingly, that such a method is feasible if, after incubation of the sample with an immobilized specific binding partner and a labeled specific detection substance, the solid phase is precipitated by means of adding a substance from the group which comprises the following substances:
i) a specific binding partner which is directed against the solid phase,
ii) a binding partner which is directed against the substance to be detected,
iii) a binding partner which is directed against an anchoring substance which is immobilized on the solid phase,
   where the antibodies are preferably of a species which is different from that of the unlabeled specific binding partner
the solid phase is centrifuged off in a current centrifugal analyzer at accelerations of from about 200 to 800× g and, for the detection, the concentration of the unused, labeled specific detection substance is determined in the supernatant.

The novel effect is probably due to the fact that precipitating the particles by means of adding "binding partners"

(see Example 4) which have a high affinity for these particles increases the sedimentation rate to such an extent that separation can take place in a current centrifugal analyzer in a short time of approximately 0.1–10 min, preferably 1–3 min. The person skilled in the art can easily, by means of suitable experiments, adjust the concentrations of the binding partners in a suitable manner, for example with a view to avoiding high-dose-hook effects.

The detection sensitivity can be improved by diluting the latex suspension (Example 5). Since, however, the concentration of the analyte/enzyme conjugate is reduced correspondingly, it may be necessary to measure the enzyme activity present in the supernatant indirectly, i.e. using additional downstream reactions(Example 6).

Distinguishing features of the novel method are the smaller number of pipetting steps, the fewer number of components which are necessary, and, in particular, the markedly shorter implementation time, which is normally in the range of from 1 to 60 min, preferably in the range of from 10 to 30 min. Thus, the novel method only requires antibodies from 2 species. Furthermore, in the novel method, measurement is carried out directly on the supernatant. In addition, this method does not require any special washing or separation devices and is therefore applicable to the current clinicochemical analyzers. Moreover, this methodological approach can be used both in competitive and in direct detection methods. Finally, this method can be used both for determining haptens and substances having only one specific epitope and also for detecting substances having several specific epitopes and is thus considerably more versatile than the previously described methods.

Depending on the determination method, labeled specific detection substances are labeled analytes in the case of competitive assays and labeled specific binding partners in the case of sandwich assays.

Labeled specific binding partners are specific binding partners which either directly carry a detectable label or else carry a group via which a label or a detection reaction can be coupled on.

Within the meaning of the invention, labeled analytes are, for example, analytes, analyte derivatives and analyte analogs which either directly carry a detectable label or else carry a group via which a label can be coupled on.

Within the meaning of the invention, labels can, for example, be enzymes, isotopes, fluorogenic or chemiluminescent groups or else stained or colored particles.

Within the meaning of the invention, specific binding partners are, for example, anti-analyte antibodies, specific lectins, receptors or similar molecules.

The following examples illustrate the invention.

EXAMPLE 1 a)

Preparation of anti-F1+2 latex reagents

Latex reagents were prepared in accordance with Kapmeyer W. H. et al., J. Clin. Lab. Anal. 2: 76–83 (1988). 1 ml of a graft polymer was mixed with 0.1 ml of antibody solution (specific rabbit antibodies against the C terminus of the F1+2 prothrombin fragment (for preparation, see EP 0 303 983; concentration: 0.5 mg/ml)) and 0.05 ml of a 20% aqueous solution of Tween® 20. In order to activate the protected aldehyde groups on the shell polymer, the suspension was adjusted to a pH of 2.5 using approximately 0.01 ml of a 1 N solution of HCl. After incubating at room temperature for 30 minutes, 25 mg of sodium borohydride were dissolved in 1 ml of a 1 M solution of sodium hydrogen phosphate (pH 6.5), and 0.25 ml of this solution was added to the coating solution. The antibody was coupled to the activated aldehyde groups at room temperature for 1 hour.

The latex/antibody conjugate was then centrifuged (Beckman centrifuge, 40,000× g, 30 minutes) and the pellet was resuspended in 1.5 ml of an 0.1 molar glycine buffer (pH 8.2; containing 0.17 M NaCl and 0.5% Tween® 20). The solution was sonicated for approximately 5 seconds (Bronson B 15 sonifier). This stock solution was stored at +4° C.

EXAMPLE 1 b)

Preparation of F1+2 peptide conjugates with alkaline phosphatase (AP) or horseradish peroxidase (POD)

a) Principle of the method

Enzyme/peptide conjugates are prepared in accordance with current principles using heterobifunctional linkers as described, for example, in P. Tijssen (Laboratory techniques in biochemistry and molecular biology; Vol. 15, Elsevier Science Publishers B. V., Asterdam-New York-Oxford, 1988). A cysteine was added to the amino terminus of the synthetically prepared antigen (F1+2 peptide; from Behringwerke AG) (see EP 0 303 983). The linkage between the SH group of the N-terminal cysteine of the peptide and the amino functions of the N-termini of the enzymes to be conjugated is effected using m-maleimidobuturyl-N-hydroxysuccinimide ester (MBS; from Serva). In order to avoid the formation of enzyme/enzyme conjugates, any free SH groups on the enzymes are protected prior to the actual coupling using N-ethylmaleimide (NEM; from Serva).

b) Preparation of SH-protected enzymes 8.8 mg of horseradish peroxidase (POD) or 15 mg of alkaline phosphatase (AP) (both from Boehringer Mannheim) are dissolved in 1 ml of coupling buffer (0.1 mol/l sodium phosphate buffer, 5 mM EDTA, pH 6.0; 1 mmol/l $MgCl_2$ and 1 $\mu$mol/l $ZnCl_2$ as well in the case of AP). 0.1 ml of NEM solution (18 mg/ml in N,N-dimethylformamide) is added dropwise at room temperature and while stirring. The vessel is sealed and incubated at room temperature for 1 hour while stirring. The solution is then dialyzed against reaction buffer (0.1 mol/l sodium phosphate buffer, pH 8.0; 1 mmol/l $MgCl_2$ and 1 $\mu$mol/l $ZnCl_2$ as well in the case of AP) and, if necessary, concentrated to approximately 1 ml in Centrikons (from Amicon; exclusion size <10 kD).

c). Insertion of a reactive maleimide function into the enzymes 0.1 ml of MBS solution (100 mg/ml m-maleimidobuturyl-N-hydroxysuccinimide ester in N,N-dimethylformamide) is added dropwise, at room temperature and while stirring, to the SH-protected enzymes in approximately 1 ml of reaction buffer from Example 1 b). The mixture is stirred for 1 hour, and the solution is dialyzed against coupling buffer (0.1 mol/l sodium phosphate buffer, 5 mM EDTA, pH 6.0; 1 mmol/l $MgCl_2$ and 1 $\mu$mol/l $ZnCl_2$ as well in the case of AP).

If necessary, the activated enzyme solutions are concentrated down to approximately 2 ml using Centrikons (from Amicon).

d) Coupling the peptide to the activated enzymes 2 mg of the F1+2 peptide are dissolved in 2 ml of coupling buffer (0.1 mol/l sodium phosphate buffer, 5 mM EDTA, pH 6.0; 1 mmol/l $MgCl_2$ and 1 $\mu$mol/l $ZnCl_2$ as well in the case of AP). 2 ml of the activated enzyme solution from Example 1b.c) are then added while stirring. The sealed vessel is incubated at room temperature for 1 hour while stirring.

e) Saturation of the remaining maleimide groups

400 $\mu$l of freshly prepared cysteine solution (10 mmol/l in 0.1 mol/l sodium phosphate buffer, 5 mM EDTA, pH 6.0; 1 mmol/l $MgCl_2$ and 1 $\mu$mol/l $ZnCl_2$ as well in the case of AP) are added to the coupling solution from Example 1b.d) and the mixture is then stirred for approximately 10 min.

f) Dialysis and storage of the F1+2 peptide/enzyme conjugate

The coupling solution from Example 1 b.e) is dialyzed against conjugate dialysis medium (5 mmol/l Tris/HCl, 0.9 g/l phenol, pH 7.4; 1 mmol/l $MgCl_2$ and 1 $\mu$mol/l $ZnCl_2$ as well in the case of AP), and stored at −20° C.

EXAMPLE 1 c)

Direct determination of F1+2 peptide using F1+2 peptide/POD conjugate

25 $\mu$l of F1+2 peptide (sample) are added to 50 $\mu$l of an anti-F1+2 latex reagent which is prepared in accordance with Example 1 and which is in a stock solution dilution of 1:30 in test medium (0.02 mol/l Tris/HCl, 9 g/l NaCl, 0.5 g/l Tween 20, pH 8.2), and this mixture is incubated at +37° C. for 15 minutes. 25 $\mu$l of an F1+2 peptide/POD conjugate (prepared in accordance with Example 1b using horseradish peroxidase; diluted 1:5000 in test medium) are then admixed and this new mixture is incubated at +37° C. for a further 10 minutes. A solution of goat anti-rabbit antibodies (from Behringwerke; 0.056 g/l in 10 mmol/l Tris/HCl, 0.45 g/l NaCl, 0.25 g/l Tween 20, 50 g/l polyethylene glycol 6000, pH 8.0) is added and the mixture is incubated at +37° C. for another 3 minutes. The precipitated particles are then separated off by centrifuging for 3 minutes at 400× g. 10 $\mu$l of the supernatant are removed and incubated with 100 $\mu$l of POD substrate solution (from Behringwerke AG) at room temperature for 30 minutes in the dark. The substrate reaction is stopped by adding 100 $\mu$l of 0.5 N sulfuric acid and the extinction is measured at 492 nm. The extinctions which were obtained in a measurement range from 1.9 to 19190 nmol/l F1+2 peptide are listed in Table 1

This experimental design was carried out in the laboratory in Eppendorf tubes. This design can also be carried out using clinicochemical centrifugal analyzers when the latter are programmed appropriately, and thus offers the possibility of being automated.

TABLE 1

The effect of the centrifugal, force applied and the duration of centrifugation, with or without precipitation of the solid phase, on the detection of F1 + 2 peptide in the novel method. G/rab IgG = goat anti-rabbit IgG antibody for precipitating the solid phase. The table lists the extinctions which were obtained in the detection reaction at 492 nm.

| Duration of centrifugation | 2 min. | | 5 min. | | 10 min. | | 5 min. | | 5 min | | 0 | |
|---|---|---|---|---|---|---|---|---|---|---|---|---|
| Centrifugal force | 200 × g | | 200 × g | | 200 × g | | 400 × g | | 800 × g | | 0 | |
| Precipitation with G/rab IgG | + | − | + | − | + | − | + | − | + | − | + | − |
| F1 + 2 peptide [nmol/l] | 0 | 0.431 | 0.682 | 0.200 | 0.468 | 0.140 | 0.312 | 0.111 | 0.266 | 0.099 | 0.185 | 1.094 | 0.993 |
| | 1.9 | 0.507 | 0.652 | 0.232 | 0.451 | 0.150 | 0.330 | 0.146 | 0.250 | 0.100 | 0.187 | 1.051 | 0.967 |

TABLE 1-continued

The effect of the centrifugal, force applied and the duration of centrifugation, with or without precipitation of the solid phase, on the detection of F1 + 2 peptide in the novel method. G/rab IgG = goat anti-rabbit IgG antibody for precipitating the solid phase. The table lists the extinctions which were obtained in the detection reaction at 492 nm.

| Duration of centrifugation | 2 min. | | 5 min. | | 10 min. | | 5 min. | | 5 min | | 0 | |
|---|---|---|---|---|---|---|---|---|---|---|---|---|
| Centrifugal force | 200 × g | | 200 × g | | 200 × g | | 400 × g | | 800 × g | | 0 | |
| Precipitation with G/rab IgG | + | − | + | − | + | − | + | − | + | − | + | − |
| 19 | 0.513 | 0.647 | 0.301 | 0.507 | 0.227 | 0.303 | 0.184 | 0.243 | 0.167 | 0.213 | 1.065 | 1.018 |
| 192 | 0.711 | 0.727 | 0.566 | 0.542 | 0.516 | 0.432 | 0.497 | 0.386 | 0.485 | 0.357 | 1.054 | 1.033 |
| 1919 | 0.955 | 0.901 | 0.893 | 0.823 | 0.890 | 0.823 | 0.869 | 0.812 | 0.868 | 0.798 | 1.053 | 1.016 |
| 19190 | 1.043 | 0.999 | 0.999 | 0.975 | 0.983 | 0.998 | 0.996 | 0.975 | 0.946 | 0.970 | 1.049 | 1.028 |

EXAMPLE 2

Increasing the analytical sensitivity by precipitating the solid phase in accordance with the invention Reference curves were plotted using F1+2 peptide in a concentration range of from 1.9 to 19190 nmol/l and employing the test design in Example 1 c). As a variation from the test design in Example 3, determinations were also carried out without precipitating the anti-F1+2 latex reagent with anti-rabbit antibodies. In addition, the centrifugation conditions were varied as regards acceleration (from 200 to 400× g) and duration (from 2 to 10 minutes). The results are summarized in Table 1.

Figure 2:
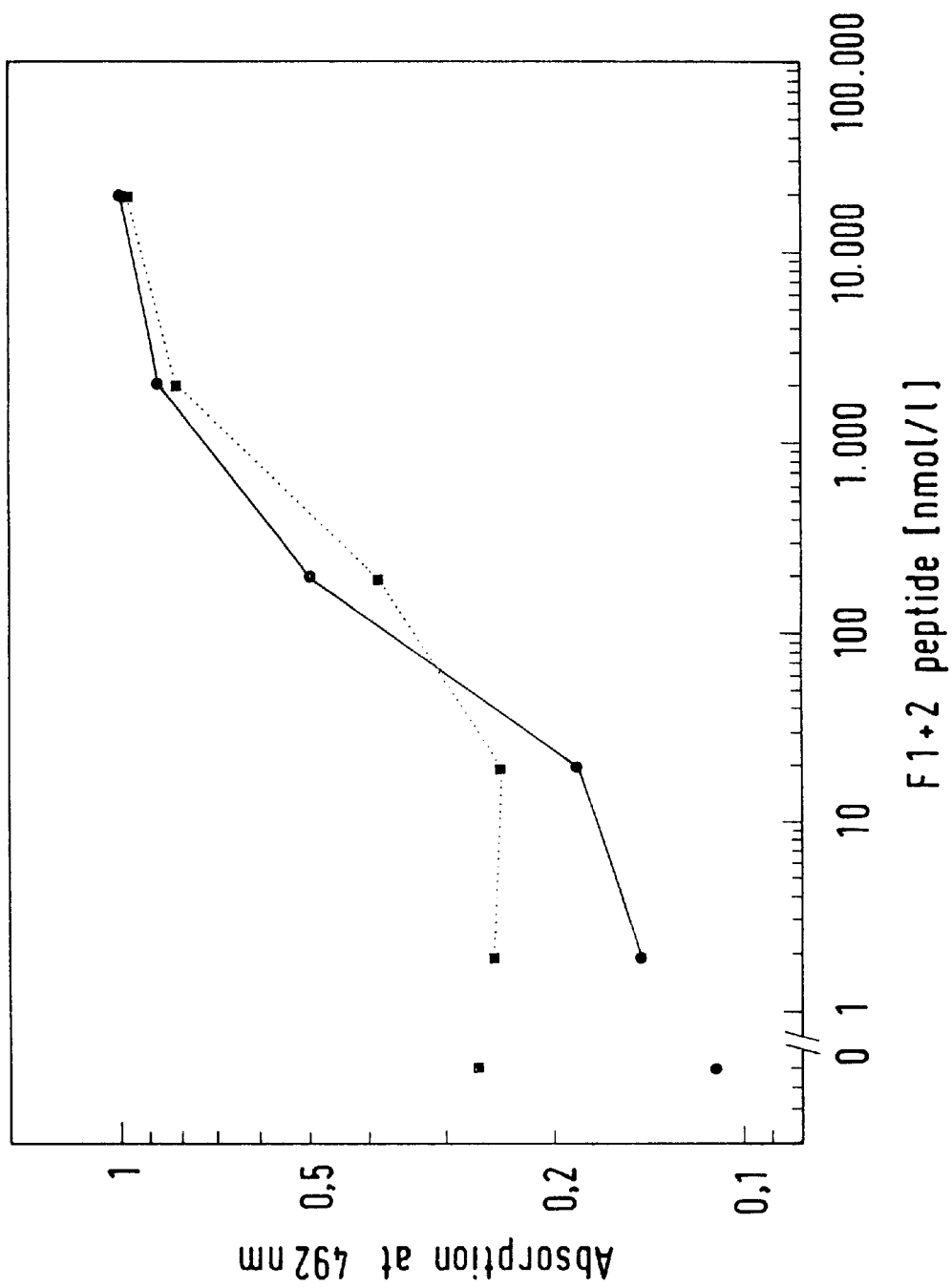
Figure 3:
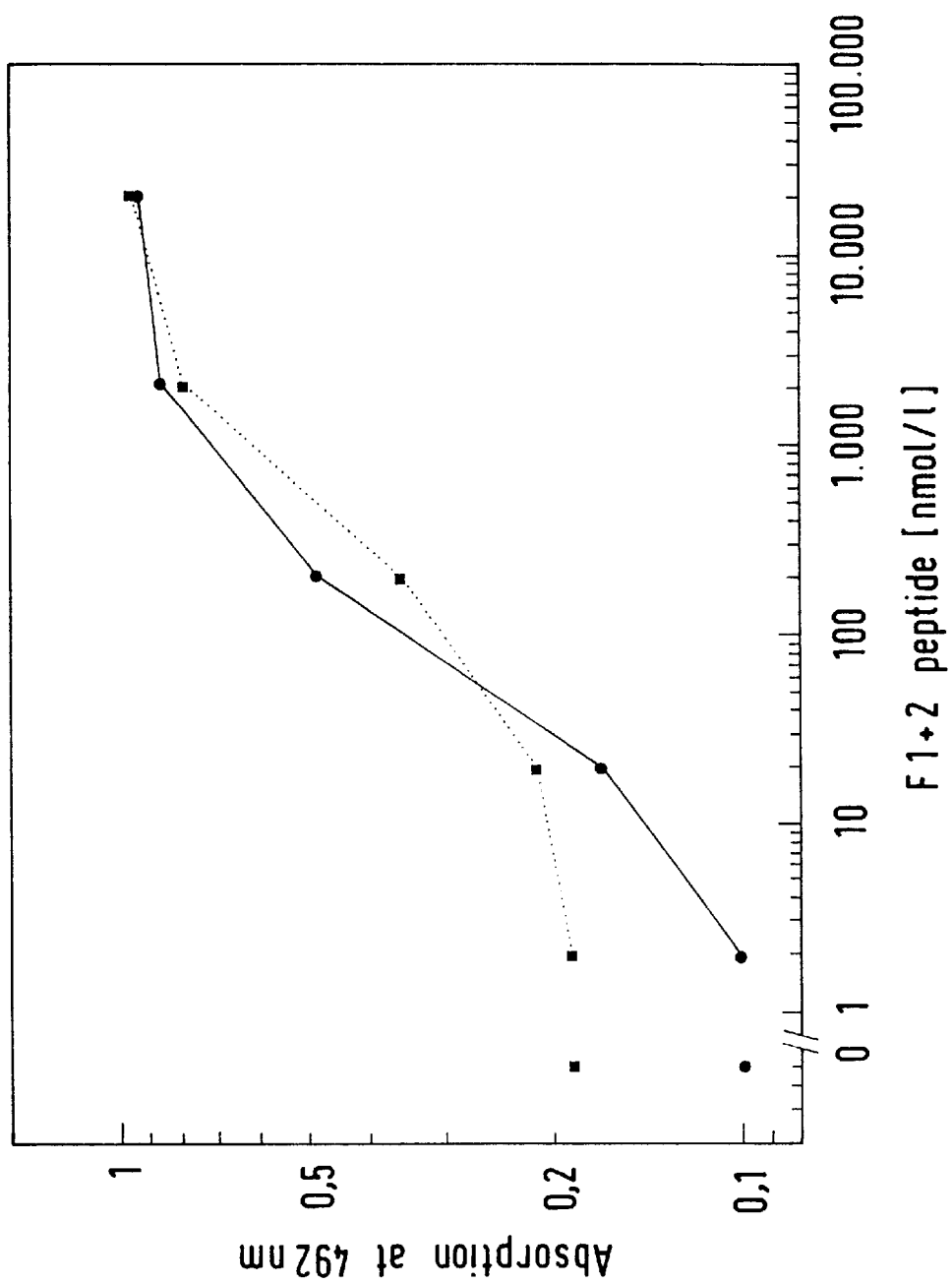

Particularly at low centrifugal accelerations, as typically obtained in clinicochemical centrifugal analyzers, it is only possible to determine F1+2 when the solid phase is precipitated in accordance with the invention (FIG. 1). The reference curves are steeper when precipitating antibodies are added, i.e. better precision and sensitivity are obtained. Furthermore, the background (without F1+2 peptide) is lower, i.e. the signal to background ratio is improved. It is also useful that there is little sedimentation in the absence of precipitating agents since the solid phase should not sediment during the incubation and mixing phases in order to ensure that the diffusion pathways for analyte and analyte/enzyme conjugate are as short as possible. However, this difference also persists at higher centrifugal accelerations (FIGS. 2 and 3). Since sedimentation is determined by the product of acceleration and time, analytical sensitivity can be achieved both by longer lasting accelerations (FIG. 4; at 200× g for from 2 to 10 minutes in the presence of precipitating antibodies) and by higher accelerations (FIG. 5, at from 200 to 800× g for 5 minutes in the presence of precipitating antibodies).

EXAMPLE 3

Adjusting the measurement range by varying the concentration of the latex reagent As a rule, the ability to increase the sensitivity and precision of the analysis by increasing the centrifugal acceleration and/or the duration of centrifugation, as described under Example 2, is limited by the design of the apparatus. Besides this, the test throughput is substantially reduced when the centrifugation times are too long. It is considerably more advantageous to alter the measurement range by reducing the amount of the latex reagent and, in connection with this, also the amount of the analyte/enzyme conjugate.

A reference curve in the range from 0.6 to 57575 nmol/l was constructed in accordance with the novel method and using F1+2 peptide. As a variation from the test design in Example 1 c), the test was carried out using anti-F1+2 latex reagent which was diluted 1:15 or 1:30 and using F1+2 peptide/POD conjugate which was diluted 1:3000 or 1:5000. In addition, the centrifugation was carried out at 3000× g. However, the substrate incubation was limited to only 15 minutes. As a result of the reactive reagents (solid phase and conjugate) being diluted to a greater extent, the measurement window, and thus the analytical sensitivity, was displaced from approximately 50–50,000 nmol/l to approximately 2–2000 nmol/l (Table 2). This is shown clearly in FIG. 6, where, due to the different conjugate concentrations, allowance was made for the background signal (0 ng/ml) in the graphic representation.

Table 2

The effect of the concentration of latex reagent (diluted 1:30 or 1:15) and of the corresponding conjugate concentration (diluted 1:5000 or 1:3000) on the detection of F1+2 peptide in the novel method.

The table lists the detection reaction extinctions at 492 nm.

| | Dilution of latex reagent | |
|---|---|---|
| | 1:30 | 1:15 |
| F1 + 2 peptide | Dilution of conjugate | |
| [nmol/l] | 1:5000 | 1:3000 |
| 0 | 0.190 | 0.110 |
| 0.6 | 0.197 | n.d. |
| 5.8 | 0.216 | n.d. |
| 58 | 0.365 | 0.129 |
| 576 | 0.612 | 0.283 |
| 5757 | 0.778 | 0.393 |
| 57576 | 0.819 | 0.405 |

EXAMPLE 4

Determination of F1+2 peptide using a downstream amplification reaction

In order to increase the analytical sensitivity, the enzyme activity remaining in the supernatant was not measured directly but, instead, was measured by the downstream insertion of an amplification reaction. The system of Harborn, St. et al. (Anal. Biochem. 206: 119–124 (1992);

PCT WO 90/01559) was used for the amplification. The system is based on cleaving phosphorylated flavine adenine dinucleotide, which can only serve as the coenzyme for an amino acid oxidase when it is in the dephosphorylated form. The activity of the amino acid oxidase is detected by the hydrogen peroxide which is released during the oxidation of the amino acid and which, for its part, serves as the substrate for an added peroxidase which transforms the substrate (4-aminoantipyrene and 3,5-dichloro-2-hydroxybenzenesulfonate), which finally yields a color reaction which is measurable at 540 nm. This color reaction is thus directly dependent on the quantity of coenzyme which is formed, which coenzyme substantially amplifies the activity of the apo-amino acid oxidase. The coenzyme is liberated by phosphatases, for which reason an F1+2 peptide/AP conjugate was, in this case, prepared as described in Example 2 and then employed in accordance with the novel method. The rest of the reagents which were required for the detection reaction were obtained, ready for use, from London Biotechnology, London.

Figure 7:
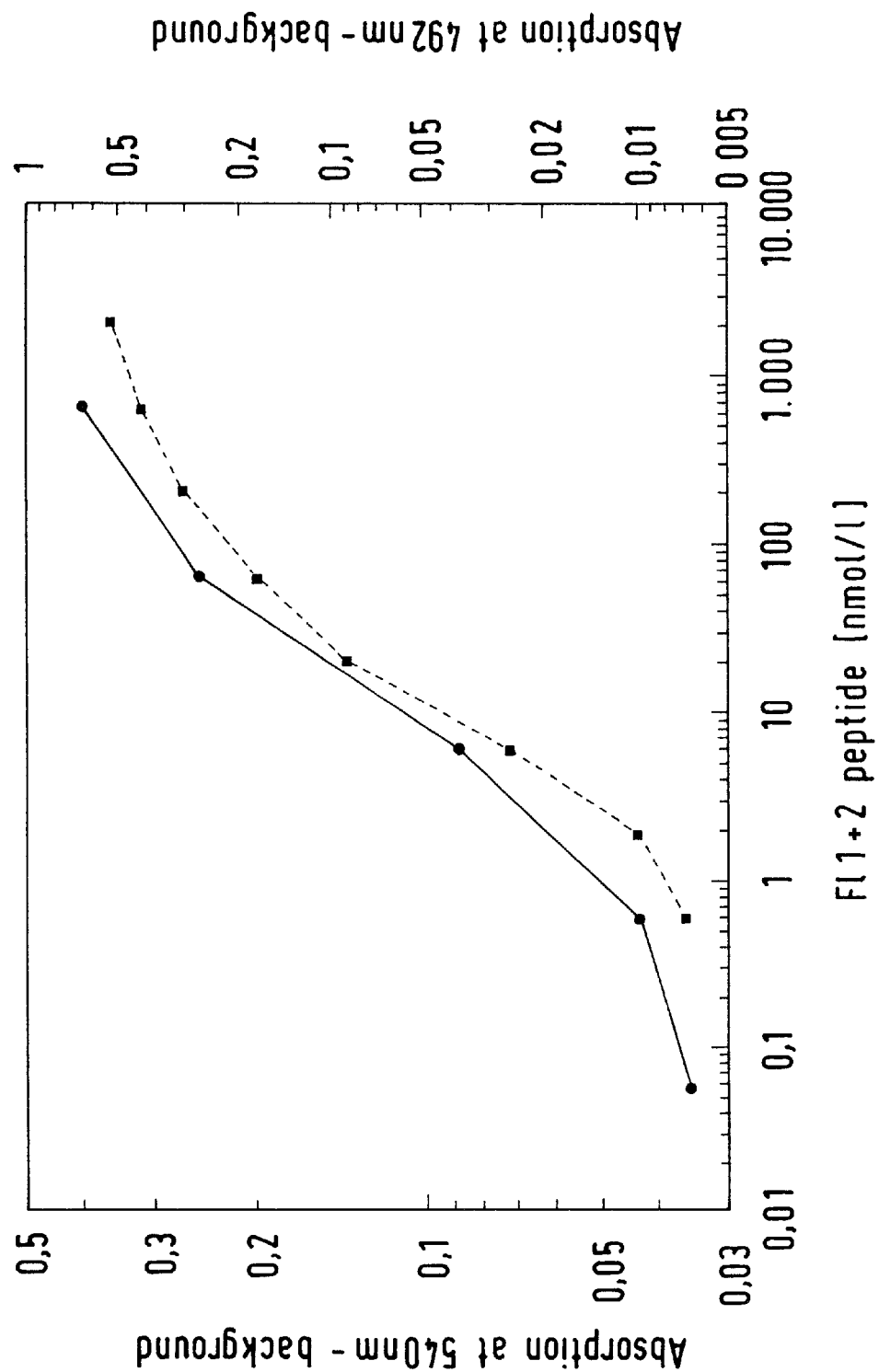

While the test was carried out as described in Example 1 c), the concentrations of anti-F1+2 latex reagent and, correspondingly, of F1+2 peptide/AP conjugate were still further reduced, as compared with Example 3, by diluting the starting solutions 1:500 and 1:10,000, respectively. The results of detecting F1+2 peptide with and without (from Example 3) amplification system, are compared in Table 3. A comparison of the results after allowance has been made for the relevant test-specific background (0 value) is depicted in FIG. 7. The use of an additional chain of reactions for detecting the conjugate remaining in the supernatant results, in this example, in an improvement in the sensitivity of detection from approximately 2 nmol/l to at least 0.2 nmol/l.

Table 3

Detection of F1+2 peptide in the novel method with and without a downstream amplification system. An F1+2/POD conjugate was used in the absence of an amplification system, and an F1+2/AP conjugate was used when the amplification system was present.
(POD=horseradish peroxidase; AP=alkaline phosphatase)

The table lists the extinctions which were obtained at 492 (POD) and 540 (AP) nm using the relevant detection system.

| F1 + 2 peptide [nmol/l] | Conjugate F1 + 2/POD absent | Amplification system F1 + 2/AP present |
|---|---|---|
| 0 | 0.190 | 0.618 |
| 0.0058 | n.d. | 0.621 |
| 0.058 | n.d. | 0.653 |
| 0.58 | 0.197 | 0.661 |
| 1.9 | 0.200 | n.d. |
| 5.8 | 0.216 | 0.706 |
| 19 | 0.279 | n.d. |
| 58 | 0.365 | 0.868 |
| 192 | 0.498 | n.d. |
| 576 | 0.612 | 1.018 |
| 1919 | 0.721 | n.d. |
| 5757 | 0.778 | 1.131 |

The figures show:

FIG. 1: Effect, in the novel method, of precipitating the solid phase with bondable ligands at a centrifugal force of 200× g and a centrifugation time of 5 minutes.

The figure shows the effect of the concentration of F1+2 peptide in the mixture on the extinctions at 492 nm obtained in the detection reaction when precipitating the solid phase in accordance with the invention (continuous line) and in the absence of precipitation (dashed line).

FIG. 2: Effect, in the novel method, of precipitating the solid phase with bondable ligands at a centrifugal force of 400× g and a centrifugation time of 5 minutes.

The figure shows the effect of the concentration of F1+2 peptide in the mixture on the extinctions at 492 nm obtained in the detection reaction when precipitating the solid phase in accordance with the invention (continuous line) and in the absence of precipitation (dashed line).

FIG. 3: Effect, in the novel method, of precipitating the solid phase with bondable ligands at a centrifugal force of 800× g and a centrifugation time of 5 minutes.

The figure shows the effect of the concentration of F1+2 peptide in the mixture on the extinctions at 492 nm obtained in the detection reaction when precipitating the solid phase in accordance with the invention (continuous line) and in the absence of precipitation (dashed line).

Figure 4:
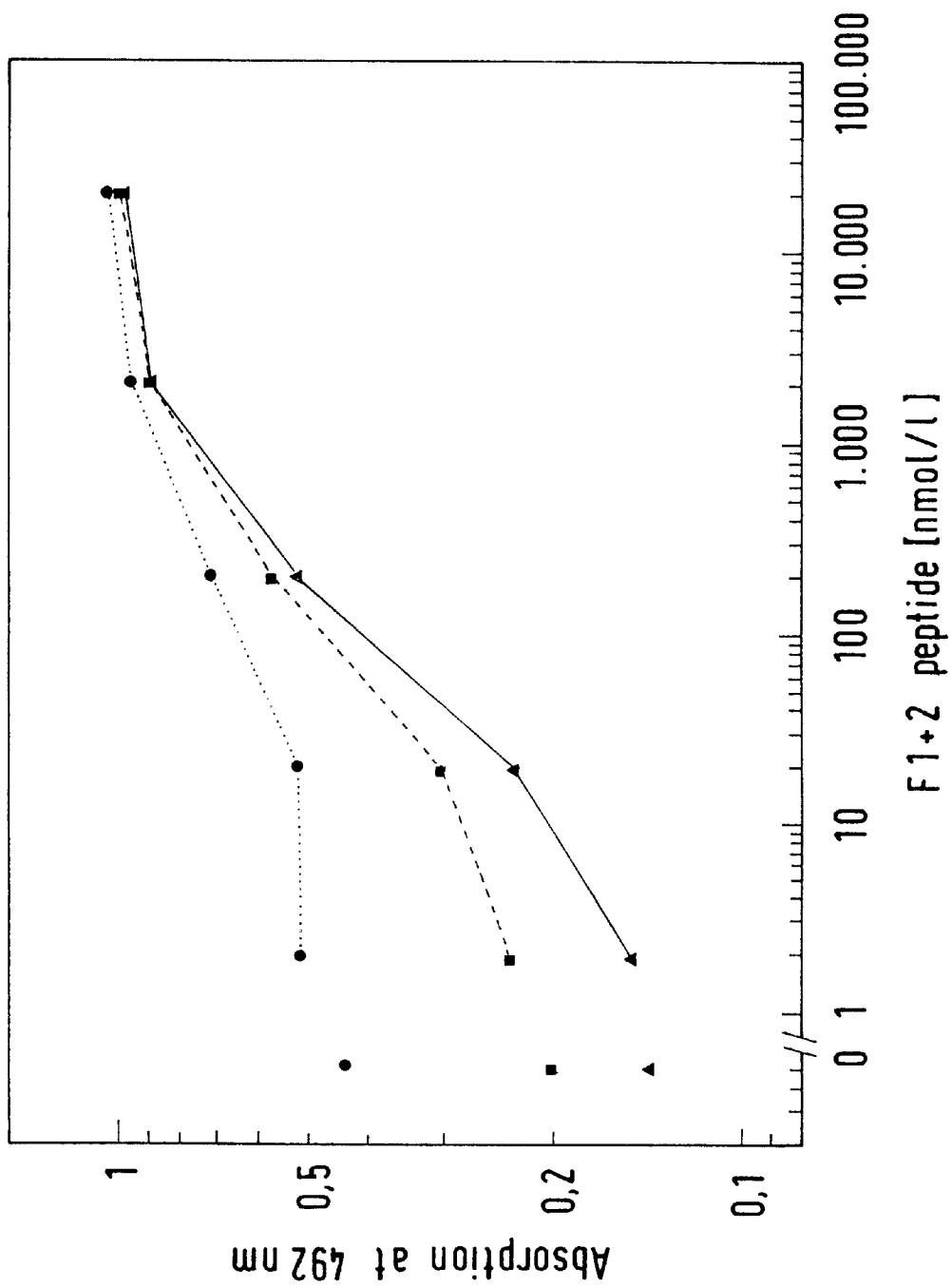

FIG. 4: Dependence of the detection reaction using F1+2 peptide, in the novel method, on the duration of centrifugation at a centrifugal force of 200× g.

The figure shows the effect of the concentration of F1+2 peptide in the mixture on the extinctions at 492 nm obtained in the detection reaction when centrifuging the precipitated solid phase for 2 minutes (dotted line), 5 minutes (dashed line) and 10 minutes (continuous line).

Figure 5:
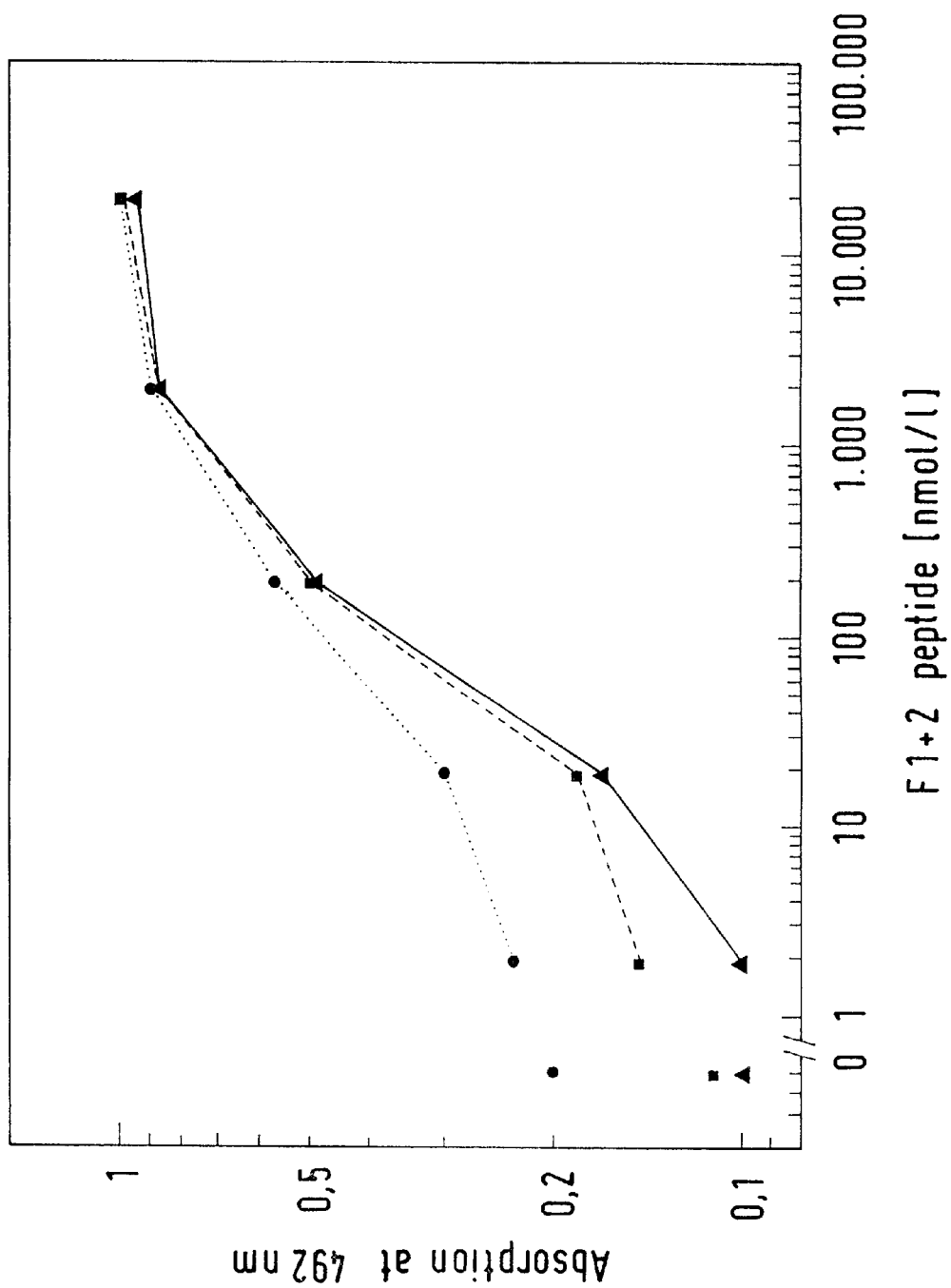

FIG. 5: Dependence of the detection reaction using F1+2 peptide, in the novel method, on the centrifugal force applied during a 5-minute centrifugation.

The figure shows the effect of the concentration of F1+2, peptide in the mixture on the extinctions at 492 nm obtained in the detection reaction when centrifuging at 200× g (dotted line), 400× g (dashed line) and 800× g (continuous line).

Figure 6:
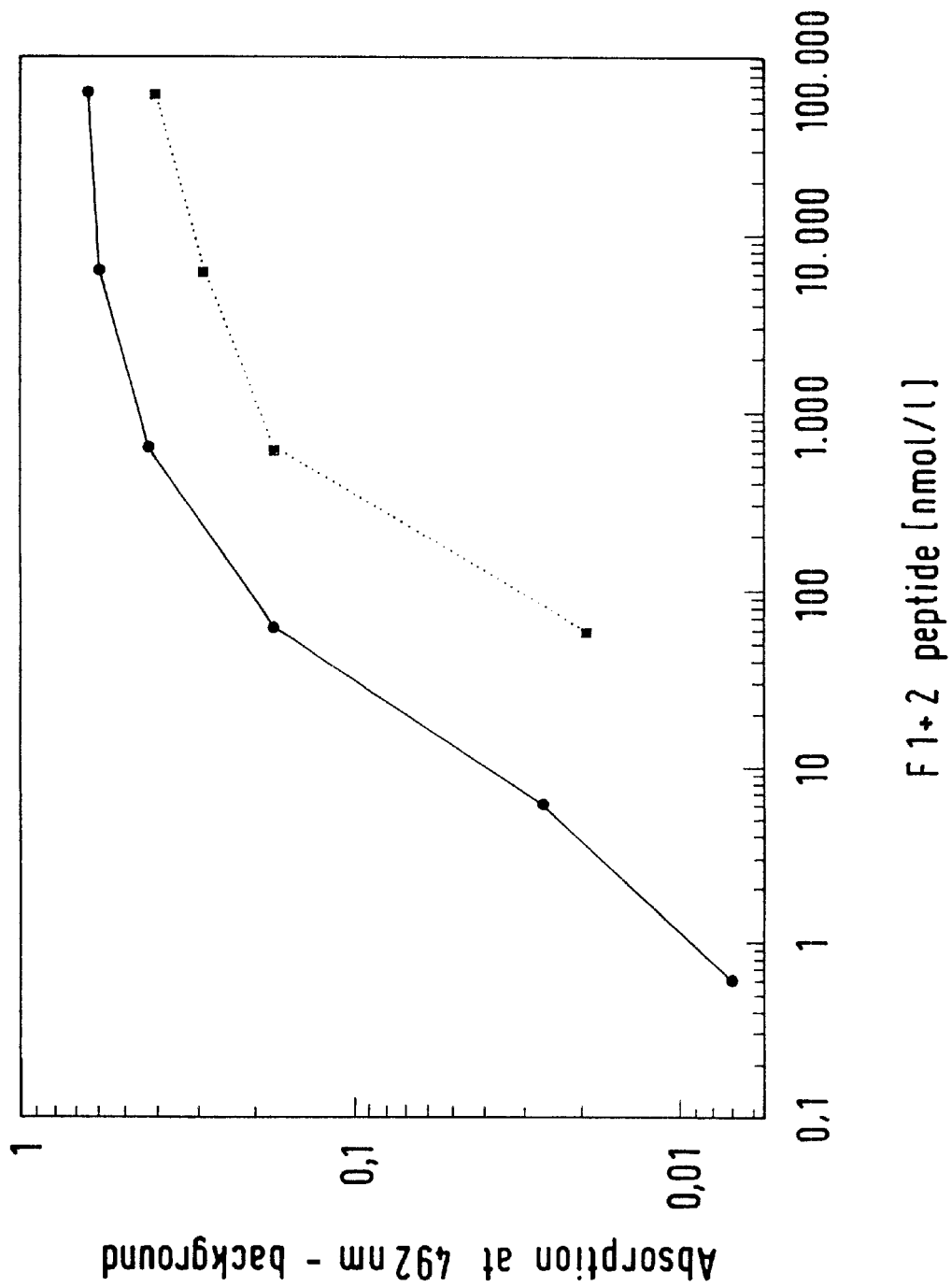

FIG. 6: Effect, in the novel method, of varying the concentration of the reactive components on the measurement window and on sensitivity for detecting F1+2 peptide.

The figure shows the effect of the concentration of F1+2 peptide in the mixture on the extinctions at 492 nm obtained in the detection reaction when using 1:30 an 1:5000 (dilute mixture; continuous line) dilutions of anti-F1+2 latex reagent and F1+2 peptide/POD conjugate, respectively, and using 1:15 and 1:3000 (concentrated mixture; dashed line) dilutions, respectively, and after having deducted the test-specific background reaction (0 ng/ml).

FIG. 7: Detection of F1+2 peptide in the novel method with and without the presence of a downstream reaction system for amplifying detection sensitivity.

The figure shows the extinctions obtained at 492 nm in an unamplified detection using F1+2 peptide/horseradish peroxidase conjugate (dashed line) and at 540 nm in an amplified detection system using F1+2 peptide/alkaline phosphatase conjugate (continuous line) after having deducted the test-specific background signal (no F1+2 peptide present in the mixture).

What is claimed is:

1. A method for the heterogeneous immunochemical detection and quantitation of an analyte in a sample of a biological fluid, which method includes the following steps
   a) immobilizing a first, unlabeled specific binding partner for the analyte on a pipettable, particulate solid phase, b) adding the sample to the immobilized, unlabeled specific binding partner, c) carrying out a first incubation of the reaction mixture, d) adding a defined quantity of a labeled, specific detection substance, e) carrying out a second incubation of the reaction mixture, f) precipitating the solid phase by adding at least one substance from the group which comprises the following precipitation substances:

i) a second specific binding partner which is directed against the solid phase, ii) a second specific binding partner which is directed against an anchoring substance which is immobilized on the solid phase, where the second specific binding partners are preferably of a species which is different from that of the first unlabeled specific binding partner, g) centrifuging the reaction mixture, h) transferring at least some of the supernatant arising in step g) to a measuring chamber, l) starting a detection reaction in the measuring chamber, and j) determining the analyte concentration from the detection reaction.

2. The method as claimed in claim 1, wherein the labeled, specific detection substance is a labeled analyte.

3. The method as claimed in claim 1, wherein the labeled, specific detection substance is at least one additional, labeled specific binding partner for the analyte.

4. The method as claimed in claim 1, wherein the analyte to be detected is a hapten or a protein having one or more specific epitopes.

5. The method as claimed in claim 4, wherein the analyte is a protein having only one specific epitope.

6. The method as claimed in claim 2, wherein the analyte has either been isolated from natural, for example animal or human, material, or else has been prepared by genetic manipulation or synthetically.

7. The method as claimed in claim 2, wherein the labeled analyte only partially corresponds to the analyte in a sample of a biological fluid, or has been chemically or biochemically modified.

8. The method as claimed in claim 1, wherein the detectable label is a radiochemically detectable element, a fluorescent or chemiluminescent compound, or an enzyme or a cofactor which is detected in an appropriate subsequent reaction.

9. The method as claimed in claim 9, wherein an enzyme, is used as the label.

10. The method as claimed in claim 1, wherein the formation of immune complexes is accelerated by adding at least one of dextran sulfate and polyethylene glycol.

11. The method as claimed in claim 2, wherein the precipitation substance is directed against the labeled analyte.

12. The method as claimed in claim 1, wherein the precipitation substance is directed against a substance which is additionally coupled to the first, unlabeled specific binding partner.

13. The method as claimed in claim 1, wherein the precipitation substance is itself immobilized on an insoluble solid phase in order to increase the speed of sedimentation.

14. The method as claimed in claim 13, wherein the first, unlabeled specific binding partner is not bound to a solid phase.

15. The method as claimed in claim 13, wherein the solid phase used for the immobilization is selected from the group of particles known per se to the person skilled in the art, such as: glass, gelatine, agarose, lipids, erythrocytes, blood platelets, leucocytes, metal colloids and synthetic materials.

16. The method as claimed in claim 15, wherein the synthetic particles are selected from the group consisting of polystyrene, polydextran, polypropylene, polyvinyl chloride, polyvinylidene fluoride, polyacrylamide or styrene-butadiene, styrene-methacrylic acid, and methacrylate-methacrylic acid copolymers.

17. The method as claimed in claim 1, wherein the precipitation substance is an antibody, lectin, avidin, streptavidin, biotin or derivatives thereof, complement factor C1, mannan-binding protein, a cofactor or another substance which enters into a specific bond with the desired reaction partner.

18. The method as claimed in claim 17, wherein the precipitation substance is an antibody.

19. The method as claimed in claim 1, wherein the precipitation reaction (f) is accelerated by altering the reaction medium.

20. The method as claimed in claim 19, wherein the precipitation reaction is accelerated by altering the pH.

21. The method as claimed in claim 1, wherein cells are employed as the pipettable, particulate solid phase, and antibodies against one or more surface antigens of these cells are employed as the precipitation substances.

22. The method as claimed in claim 1, wherein magnetizable particles are employed as the pipettable, particulate solid phase, and magnetic particles are employed as the precipitation substances, or, in the reverse method, magnetic particles are used as the solid phase, and other magnetic or magnetizable particles are used for the precipitation.

23. The method as claimed in claim 3, wherein the additional, labeled specific binding partner comprises at least one of the following substances: antibody, lectin, avidin, streptavidin, biotin, or derivatives thereof, complement factor C1, mannan-binding protein or a cofactor.

24. The method as claimed in claim 9, wherein the enzyme is alkaline phosphatase or horseradish peroxidase.

25. The method as claimed in claim 15, wherein the metal colloids and the synthetic materials are magnetizable.

* * * * *